United States Patent [19]
Glenn

[11] 4,325,381
[45] Apr. 20, 1982

[54] ULTRASONIC SCANNING HEAD WITH REDUCED GEOMETRICAL DISTORTION

[75] Inventor: William E. Glenn, Fort Lauderdale, Fla.

[73] Assignee: New York Institute of Technology, Old Westbury, N.Y.

[21] Appl. No.: 96,322

[22] Filed: Nov. 21, 1979

[51] Int. Cl.³ .............................................. A61B 10/00
[52] U.S. Cl. ...................................... 128/660; 73/620
[58] Field of Search ................................ 367/150–151; 310/335; 73/620, 627, 629, 642, 644; 128/660–663

[56] References Cited

U.S. PATENT DOCUMENTS

| | | | |
|---|---|---|---|
| 3,168,659 | 2/1965 | Bayre et al. | 367/150 |
| 3,387,604 | 6/1968 | Erikson | 310/335 |
| 3,800,276 | 3/1974 | Rishell | 367/10 |
| 3,927,557 | 12/1975 | Viertl | 73/642 |
| 4,084,582 | 4/1978 | Nigam | 367/151 |
| 4,131,022 | 12/1978 | Mezrich | 128/660 |
| 4,168,482 | 9/1979 | Sternberg | 367/150 |
| 4,185,501 | 1/1980 | Proudian et al. | 128/660 X |
| 4,217,516 | 8/1980 | Iinuma et al. | 128/660 |

FOREIGN PATENT DOCUMENTS 2017302  10/1979  United Kingdom .

OTHER PUBLICATIONS

Ardenne, M. et al., "Ultraschall-Focoscan-Anlage zur Aufnahme von A-, B-, C-und 3D-Bildern in der medizinischen Ultraschall-Diagnostik", Nachrichtentechnik-18 (1968).

*Primary Examiner*—Robert W. Michell
*Assistant Examiner*—Francis J. Jaworski
*Attorney, Agent, or Firm*—Martin Novack

[57] ABSTRACT

An improved ultrasonic scanning head is disclosed for use in an apparatus for imaging sections of a body by transmitting ultrasonic energy into the body and determining the characteristics of the ultrasonic energy reflected therefrom. The scanning head includes a scanning window which comprises an acoustic lens for converging the scan of the ultrasound beam. This serves to reduce geometrical distortion.

13 Claims, 5 Drawing Figures

ULTRASONIC SCANNING HEAD WITH REDUCED GEOMETRICAL DISTORTION

BACKGROUND OF THE INVENTION

This invention relates to apparatus for imaging sections of a body by transmitting ultrasonic energy into the body and determining the characteristics of the ultrasonic energy reflected therefrom and, more particularly, to an improved ultrasonic scanning head for such apparatus.

In recent years ultrasonic techniques have become more prevalent in clinical diagnosis. Such techniques have been utilized for some time in the field of obstetrics, neurology and cardiology, and are becoming increasingly important in the visualization of a number of different body portions, for example, the scanning of breasts to detect tumors.

Various fundamental factors have given rise to the increased use of ultrasonic techniques. Ultrasound differs from other forms of radiation in its interaction with living systems in that is has the nature of a mechanical wave. Accordingly, information is available from its use which is of a different nature than that obtained by other methods and it is found to be complementary to other diagnostic methods, such as those employing X-rays. Also, the risk of tissue damage using ultrasound appears to be much less than the apparent risk associated with ionizing radiations such as X-rays.

The majority of diagnostic techniques using ultrasound are based on the pulse-echo method wherein pulses of ultrasonic energy are periodically generated by a suitable piezoelectric transducer such as a lead zirconate-titanate ceramic. Each short pulse of ultrasonic energy is focused to a narrow beam which is transmitted into the patient's body wherein it eventually encounters interfaces between various different structures of the body. When there is a characteristic impedence mismatch at an interface, a portion of the ultrasonic energy is reflected at the boundary back toward the transducer. After generation of the pulse, the transducer operates in a "listening" mode wherein it converts received reflected energy or "echoes" from the body back into electrical signals. The time of arrival of these echoes depends on the ranges of the interfaces encountered and the propagation velocity of the ultrasound. Also, the amplitude of the echo is indicative of the reflection properties of the interface and, accordingly, of the nature of the characteristic structures forming the interface.

There are various ways in which the information in the received echoes can be usefully presented. In one common technique, the electrical signal representative of detected echoes are amplified and applied to the vertical deflection plates of a cathode ray display. The output of a time-base generator is applied to the horizontal deflection plates. Continuous repetition of the pulse/echo process in synchronism with the time-base signals produces a continuous display, called an "A-scan," in which time is proportional to range, and deflections in the vertical direction represent the presence of interfaces. The height of these vertical deflections is representative of echo strength.

Another common form of display is the so-called "B-scan" wherein the echo information is of a form more similar to conventional television display; i.e., the received echo signals are utilized to modulate the brightness of the display at each point scanned. This type of display is found especially useful when the ultrasonic energy is scanned transverse the body so that individual "ranging" information yields individual scan lines on the display, and successive transverse positions are utilized to obtain successive scan lines on the display. The two-dimensional B-scan technique yields a cross-sectional picture in the plane of the scan, and the resultant display can be viewed directly or recorded photographically or on magnetic tape.

While successes have been achieved in the field of ultrasonic imaging, there are a number of problems which need to be overcome in obtaining high quality untrasonic images in a convenient, reliable and cost-effective manner. Regarding problems which have been partially overcome, it is known, for example, that ultrasound is almost totally reflected at interfaces with gas. This has led to the use of coupling through a fluid such as water or the use of a direct-contact type of transducer. The latter technique may give rise to problems when attempting to image structures such as arteries which may be only a few millimeters below the skin surface, the contact imaging causing aberrations in the near field of the transducer. Coupling through a fluid offers advantage over direct-contact in this respect, but, until recently, lead to various design problems and cumbersome generally nonportable structures which were inconvenient to use, especially when attempting to register them accurately on a patient. Some techniques involve immersing the patient in water or obtaining appropriate contact of the body part with a bulky water tank wall.

The need to scan the ultrasonic beam in two dimensions gives rise to problems of bulkiness and difficulty of handling in the scanning unit. In the U.S. Pat. No. 4,084,582, there is disclosed a type of apparatus which provides improved convenience as compared to most water coupled imaging techniques. The apparatus disclosed therein has a console which typically includes a timing signal generator, energizing and receiving circuitry, and a display/recorder for displaying and/or recording image-representative electronic signals. A portable scanning head or module, suitable for being hand held, has a fluid-tight enclosure having a scanning window formed of a flexible material. A transducer in the portable scanning module converts energy from the energizing circuitry to ultrasonic energy and also converts received ultrasound echoes back into electrical signals which are coupled to the receiver circuitry. A focusing lens is coupled to the transducer, and a fluid, such as water, fills the portable scanning module in the region between the focusing lens and the scanning window. A reflective scanning mirror is disposed in the fluid, and a driving motor, energized in synchronism with the timing signals, drives the scanning mirror in periodic fashion. The ultrasound beam is reflected off the scanning mirror and into the body being examined via the scanning window. Improved versions of the scanning head are set forth in my copending U.S. application Ser. Nos. 890,377 and 890,378, assigned to the same assignee as the present application. The scanning head disclosed in these copending applications has, among other features, a scanning window formed of a rigid material.

For a two dimensional B-scan taken with the referenced type of scanning head, the dimensions scanned are: (1) depth into the body, which varies during each display scanline by virtue of the ultrasound beam travelling deeper into the body as time passes; and (2) a slower transverse scan caused by the scanning mirror. The display is typically in a rectangular format, e.g., the familiar television type of display with linear sweeps in both directions. However, the transverse scan of the ultrasound beam itself, as implemented by the scanning mirror, results in a sector scan. For distances deeper in the body, the fanning out of the sectors results in geometrical distortion when displayed on a linear rectangular display. For example, the azimuth dimension in the extreme far field may be, say 2½ times larger than the azimuth dimension in the extreme near field. Thus, the density of information on the left-hand side of a conventional left-to-right display is much higher than the density of information on the right-hand side of the display. In other words, what appear to be equal distances in the body on the left and right hand sides of the display are actually substantially different distances.

It is among the objects of the present invention to provide a solution to the problem of geometrical distortion, as set forth below.

SUMMARY OF THE INVENTION

The present invention is applicable for use in an apparatus for ultrasonically imaging sections of the body by transmitting ultrasonic energy into the body and determining the characteristics of the ultrasonic energy reflected therefrom. The apparatus typically includes timing means for generating timing signals, and energizing/receiving means (which may be a separate energizer and receiver, or a single unit) operative in response to timing signals. The apparatus also typically includes display/record means synchronized with the timing signals for displaying and/or recording image-representative signals from the energizing/receiving means. In accordance with the invention, an improved portable scanning module is set forth and includes a fluid-tight enclosure having an ultrasonically-transmissive scanning window which can be placed in contact with the body. A fluid is contained in the enclosure. Transducer means, coupled to the energizing/receiving means, are provided for converting electrical energy to a beam of ultrasonic energy and for converting reflected ultrasonic energy to electrical signals. Means are provided for focusing the ultrasound beam emanating from the transducer means. A reflective scanning means is pivotably mounted in the fluid in the path of the ultrasound beam, and is operative to effect scanning of the beam across the body via the window. In accordance with the principles of the invention, the scanning window comprises an acoustic lens for converging the scan of the ultrasound beam incident thereon from within the enclosure. The acoustic lens thereby serves to reduce geometric distortion of the scan of the ultrasound beam.

In the preferred embodiment of the invention, the window/lens is formed of a rigid plastic material in a substantially plano-concave shape, with the concave surface facing the outside of the enclosure. In this embodiment, the window/lens is provided with a focal length of between one and two times the distance between the reflective scanning means and the window/lens. A focal length of about one-and-a-half times the distance between the reflective scanning means and the window/lens is considered particularly suitable in a presently functioning embodiment.

Further features and advantages of the invention will become more readily apparent from the following detailed description when taken in conjunction with the accompanying drawings.

DESCRIPTION OF THE PREFERRED EMBODIMENT

Figure 1:
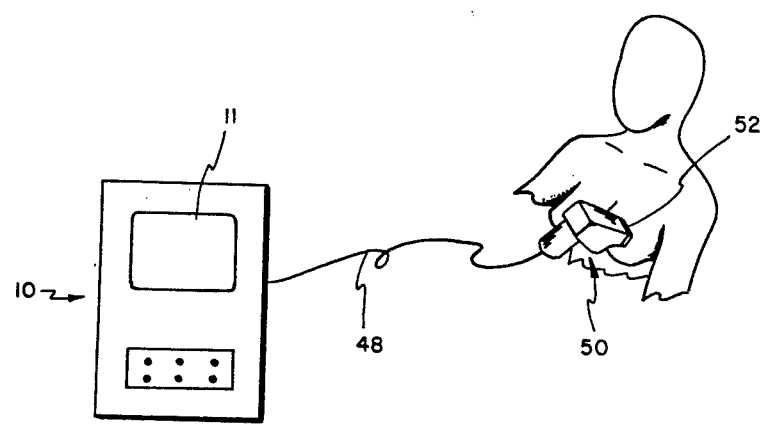
FIG. 1 is a scanning apparatus which employs the improvements of the invention.

Referring to FIG. 1, there is shown an illustration of a scanning apparatus which employs the improvements of the invention. A console 10 is provided with a display 11 which may typically be a cathode ray tube television-type display, and suitable control panel. A video tape recorder or suitable photographic means may also be included in the console to effect ultimate display of images. The console will typically house power supplies and portions of the timing and processing circuitry of the system to be described. A portable scanning module or probe 50 is coupled to the console by a cable 48. The probe has a generally cylindrical handle and a scanning window 52 near one end. During operation of the apparatus, the probe 50 is hand-held to position the scanning window over a part of the body to be imaged. For example, in FIG. 1 the probe is positioned such that a cross-section of the breast will be obtained. Imaging of other portions of the body is readily attained by moving the probe to the desired position and orientation, the relative orientation of the scanning window determining the angle of the cross-section taken.

Figure 2:
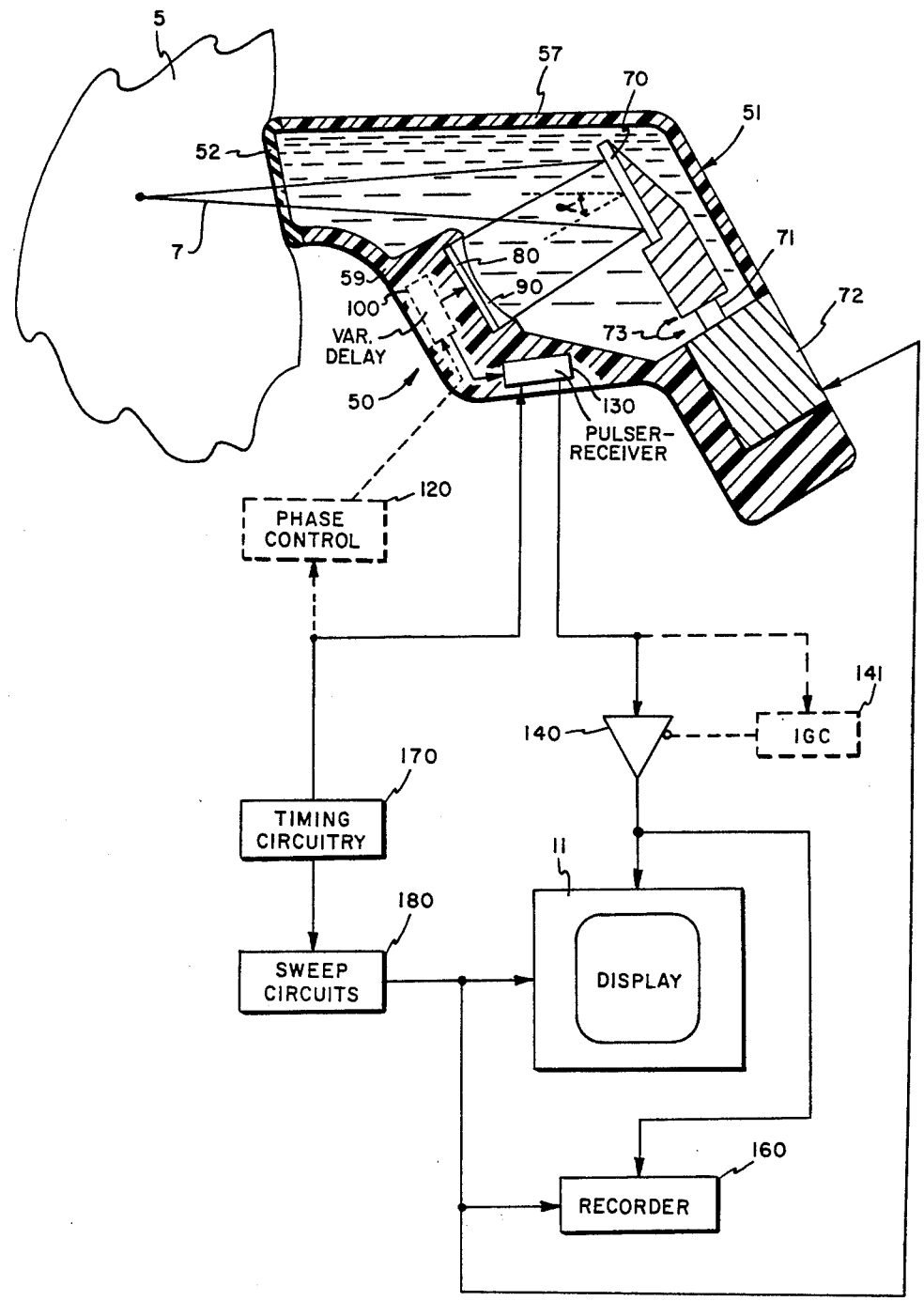
FIG. 2 is a cross-sectional view of a scanning module as set forth in applicant's prior copending U.S. applications.

To aid in understanding the invention, reference is initially made to FIG. 2 which shows a cross-sectional view of the scanning module or probe 50 as it is set forth in my above-referenced copending U.S. applications Ser. Nos. 890,377 and 890,378, along with diagrams of portions of the circuitry therein and in console 10 used in conjunction therewith. An enclosure 51, which may be formed of a sturdy plastic, has scanning window 52 at the front end thereof. The enclosure 51 is filled with a suitable fluid 57, for example, water. The scanning window 52 is described in the copending applications as being relatively flat and formed, for example, of polystyrene or nylon. A reflective scanning mirror 70 is positioned at the approximate rear of the enclosure 51 and substantially faces the window 52. The scanner 70 is mounted on a shaft 71 which passes through a suitable seal and is connected to an electric motor 72 which is mounted in a recess in enclosure 51 and is driven to provide the desired oscillatory motion of scanner 70, as depicted by curved two-headed arrow 73.

An ultrasonic transducer 80, which may have an associated focusing lens 90, is mounted in a compartment 59 of enclosure 51. The transducer is mounted relatively frontwardly of reflective scanner 70 in the module 50 with the ultrasound-emitting face of the transducer generally facing rearwardly in the module 50 and being directed toward the reflective scanner 70.

As described in my above-referenced copending U.S. applications, the transducers 80 is positioned such that the ultrasound beam which it emits is reflected by the scanner 70 to double back past transducer 80 before passing through the window 52. The scanner preferably has a reflective surface formed of a material which results in a relatively small critical angle so that the beam impinging almost directly on the reflector surface will not pass through the reflector. The described arrangement makes efficient use of the volume of fluid 57 in the module 50 since the beam 7 is effectively "doubling back" past the transducer and experiencing a relatively large travel distance through a relatively small volume of water.

A pulser/receiver circuit 130 alternatively provides energizing pulses to and receives echo signals from the transducer 80. As used herein, the term pulser/receiver is intended to include any combined or separate circuits for producing the energizing signals for the transducer and receiving echo signals therefrom. If dynamic focusing is employed, the transducer 80 may be segmented and the pulser/receiver circuitry 130 may be coupled to the segments of transducer 80 via variable delay circuitry 100, shown in dashed line. The pulser/receiver circuitry 130 and the variable delay circuitry 100 (if present) are typically, although not necessarily, located in the scanning module 50, for example, within the compartment 59. The receiver portion of circuit 130 is coupled through an amplifier 140 to display 11 and to recorder 160, which may be any suitable recording, memory, and/or photographic means, for example, a video tape recorder. If desired, gain control circuitry including an interactive gain compensation ("IGC") capability, as represented by the block 141 (shown in dashed line), can be employed. Interactive gain compensation techniques are described in detail in the copending U.S. Pat. No. 4,043,181, assigned to the same assignee as the present application. This circuitry compensates the amplitude of later arriving signals for attention experienced during passage through body tissue and losses due to prior reflections. Accordingly, if an IGC capability is employed, the amplifier 140 may be used as a gain control amplifier under control of an IGC signal from circuit 141. Timing circuitry 170 generates timing signals which synchronize operation of the system, the timing signals being coupled to pulser/receiver 130 and also to sweep circuitry 180 which generates the signals that control the oscillations of scanner 70 and the vertical and horizontal sync signals for the display 11 and recorder 160. If dynamic focusing is employed, the timing signals may also be coupled to phase control circuitry 120 which produces signals that control the variation of the delays in variable delay circuit 100. Also, a lens 90, which typically has a relatively flat surface bonded to the transducer and a curved concave surface which provides focusing of the beam emanating from the transducer may be employed in the scanning module 50. If desired, however, alternative means of focusing can be employed, such as electronic focusing using a segmented transducer, or providing curvature in the transducer or reflector surface.

Operation of the system is as follows: Upon command from the timing circuits the pulser in circuitry 130 generates pulses which excite the transducer 80, the segments of transducer 80 being excited via variable delay circuitry 100, under control of phase control circuitry, when dynamic focusing is employed. (As is known in the art, the depth of focus can be varied electronically in a dynamically focused system by imparting predetermined delays or phase changes to different segments of the transducer 80. In such case the ultrasound pulse is typically launched with the variable delay circuitry set so that the transmitted beam is focused at a point which is between the center of the field and the deepest point within the body at which an image is being sought.) The beam of ultrasound resulting from pulsing the transducer is reflected by reflector 70 through the window 52 and into the body 5. The timing circuitry now causes the pulser/receiver 130 to switch into a "receive" or "listen" mode. (If dynamic focusing is employed, a cycle of the phase control circuitry 120 is activated.) Now, as the ultrasound echoes are received from the body via window 52 and reflected off scanner 70 toward transducer 80, the transducer serves to convert the received ultrasound energy into electrical signals. (Again, for a dynamic focusing implementation, the transducer segments serve to convert the received ultrasonic energy into electrical signals which are combined in proper phase relationship for focusing on particular reflection origination points in the range of depths being investigated.) For a two-dimensional "B-scan" display, a sweep over the range of depth corresponds to a horizontal scanline of the display, so the timing signals from circuitry 170 synchronize the horizontal sync of the display such that the active portion of one scanline of the display corresponds to the time of arrival of echoes from a given range within the body 5, typically from the patient's skin up to a fixed preselected depth in the body. The second dimension of the desired cross-sectional image is attained by the slower mechanical scan of reflective scanner 70 which is synchronized with the vertical sweep rate of the display and recorder by the sweep circuitry 180. The received signals are coupled through amplifier 140 to display 11 wherein the received signals modulate the brightness of the scanning raster to obtain the desired cross-sectional image, with each scanline of the television-type display representing a depth echo profile of the body for a particular angular orientation of the scanner 70. The received signals can also be recorded on video tape recorder 160. As disclosed in my above-referenced copending U.S. applications, the transducer 80 may have a generally elliptical shape and is preferably elongated along the directin of the scan. The reflector 70 and window 52 can also be elongated along the direction of the scan.

Figure 3:
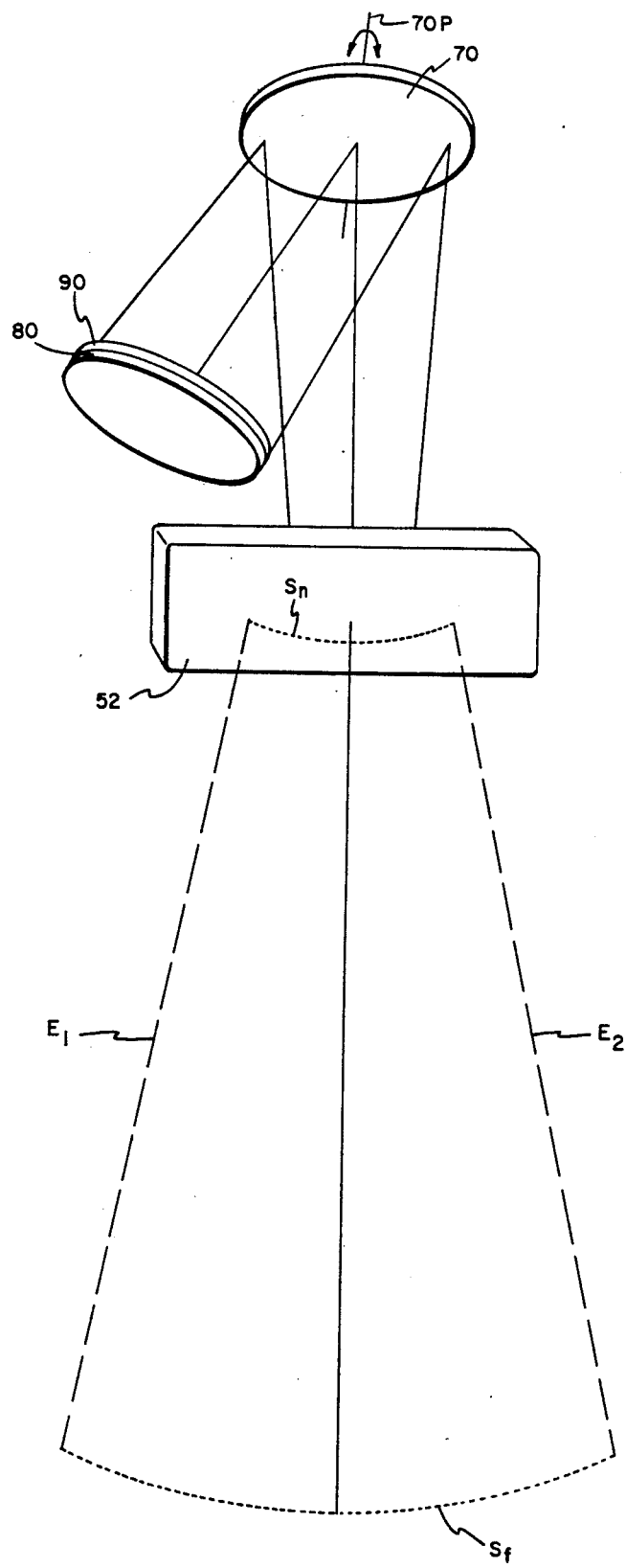
FIG. 3 illustrates the type of scan that is obtained with the scanning module of FIG. 2.

Referring to FIG. 3, there is illustrated the type of scan that is obtained with the scanning module of FIG. 2; i.e., with a window 52 that does not provide a converging focus of the ultrasound beam. For ease of illustration, only the central ray of the ultrasound beam (which is reflected off the approximate pivot axis 70P of oscillating reflector 70) is shown in the region outside the window 52. The extremes of scan of the central ray (which occur at the oscillation extremes of reflector 72) are illustrated by the dashed lines $E_1$ and $E_2$. The dotted lines $S_n$ and $S_f$ respectively represent the scanning path traversed at an extreme near field point and an extreme far field point. It can be seen that the distance traversed per scan is much greater in the far field than in the near field, for example, a ratio $S_f:S_n$ of about 2.5:1 in the present illustrative case. This results in the type of geometric distortion referred to in the background portion hereof.

Figure 4:
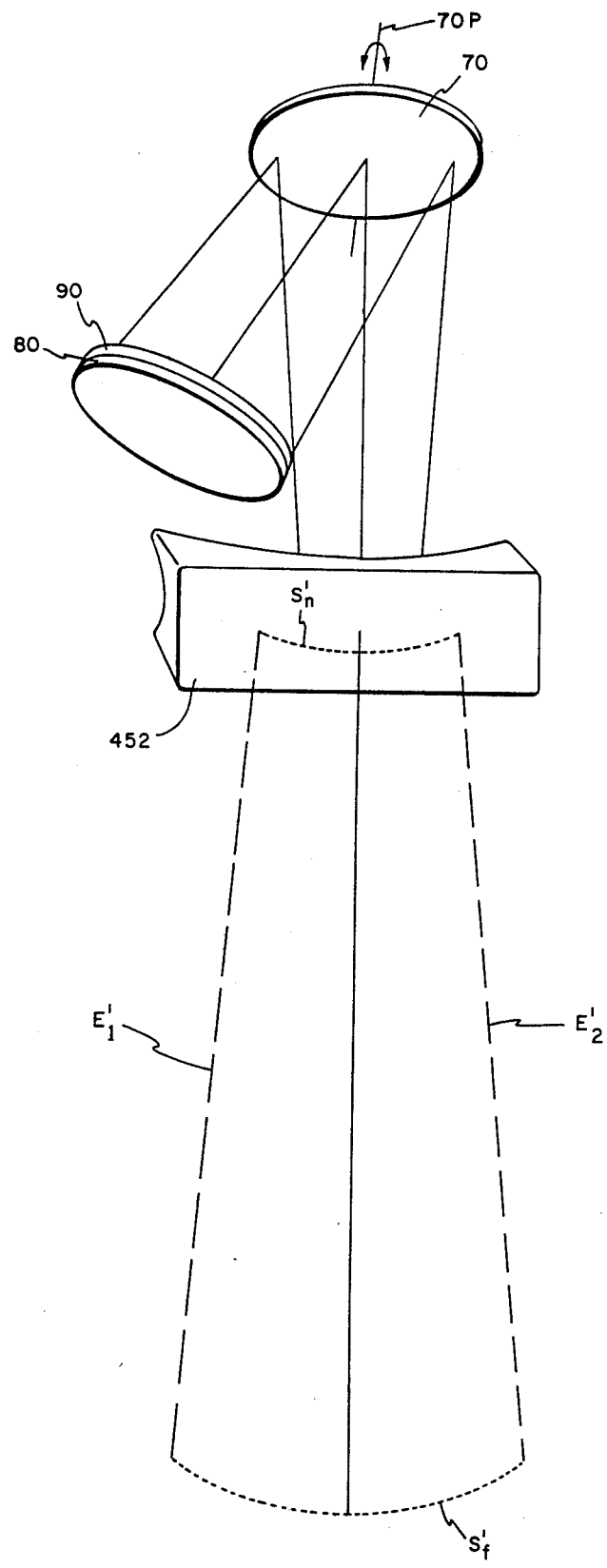
FIG. 4 illustrates a window that serves as an acoustic lens in accordance with the invention, and illustrates the type of scan that is obtained therefrom.

Referring to FIG. 4, there is shown a window 452 in accordance with the invention, the window in this case comprising an acoustic converging lens. In the present embodiment, the lens is formed of a plastic material such as a polystyrene. The lens preferably has an elliptical contour, consistent with the principles set forth in U.S. Pat. No. 3,958,559, and is preferably axially symmetrical. Except for the window 452, the scanning head or module 50 may be similar to the scanning module illustrated in FIG. 2. In the embodiment of FIG. 4, the window/lens 452 is a plano-concave lens with the concave surface thereof facing the inside of the enclosure 51. As in FIG. 3, only the central ray of the ultrasound beam is shown in the region beyond the window. The extremes of scan of the central ray are gaing shown in dashed line, labelled $E_1'$ and $E_2'$. The dotted lines $S_n'$ and $S_f'$ respectively represent the scanning path traversed at an extreme near field point and an extreme far field point. It is seen that, in this case, the convergence of the beam by virtue of the acoustic lens 452 results in a substantial reduction of geometrical distortion as compared to the situation of FIG. 3.

Figure 5:
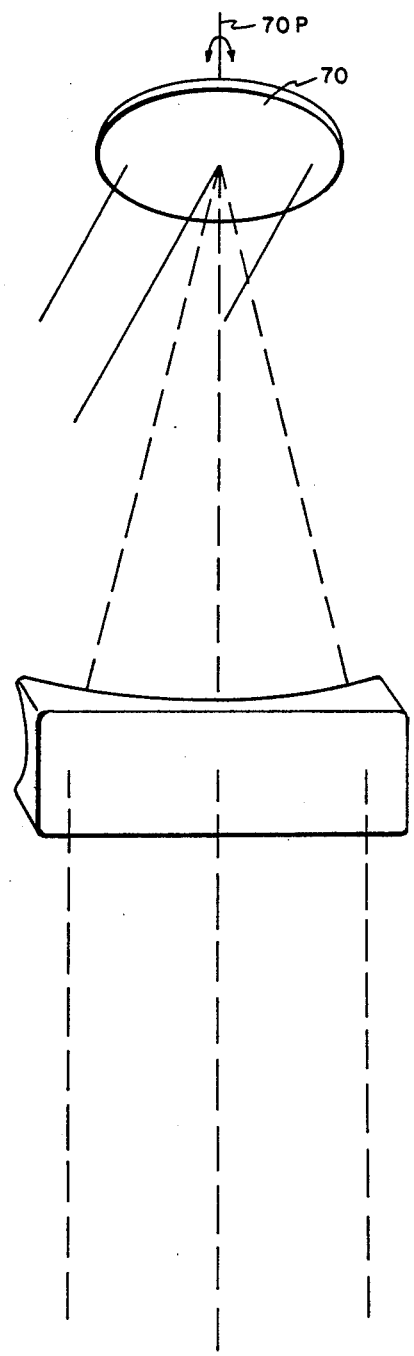
FIG. 5 is useful in understanding the relationship between the focal length of the window/lens and the resultant scan pattern.

In the arrangement illustrated in FIG. 4, the focal length of acoustic lens 452 is selected as being longer than the distance between the scanning reflector 70 and the acoustic lens 452. The preferred range for the focal length of acoustic lens 452 is between about 1 and 2 times the distance between the reflective scanner and the acoustic lens, and in the FIG. 4 embodiment, the focal length is selected to be about 1½ times the distance between the reflective scanner 70 and the acoustic lens 452. It will be understood that geometric distortion can be largely eliminated if one selects the focal length of acoustic lens 452 to be approximately equal to the distance between the scanning reflector 70 and the acoustic lens 452. This is illustrated in FIG. 5, which shows the central ray of the ultrasound beam from the transducer and the range of scan of this central ray (dashed lines $E_1''$ and $E_2''$) at the extremes of the scanning reflector oscillation. Since in this case the pivot axis of the scanning reflector is selected as being at about the focal point of the acoustic lens, it is seen that the central ray of the beam will always be approximately parallel as it leaves the acoustic lens; i.e., geometric distortion will be practically eliminated. However, certain practical operating considerations, to be discussed, indicate that selecting the focal length of the acoustic lens as being longer than the distance between the scanning reflector and the lens is probably advantageous from an overall standpoint.

In addition to reducing or eliminating geometrical distortion, the present invention has the advantage of increasing the effective aperture in the far field, and thereby enhancing the far field resolution and sensitivity. This can be understood by recognizing that the window/lens tends to equalize the focused spot size (which would normally become larger as the beam goes deeper into the body being investigated). The window/lens also tends to move the geometric focus closer to the center of the field of view than would be the case in its absence, so the frequency range of a clock used in generating dynamic focusing can be reduced. A further advantage of the present invention, when used in conjunction with dynamic focusing, is that the difference in the delays associated with the various segments of the transducer are approximately linear as a function of time (i.e., as the spot being examined moves deeper into the body).

Having listed advantages of the invention, it should be noted that there are some accompanying disadvantages which can be ameliorated by making certain operational trade-offs. To obtain, in the far field, the same effective angular scanning range as a comparable system without the window/lens, the scan angle of the present unit would have to be increased. Also, if dynamic focusing is used, the dynamic focusing focal length in the far field should be increased. (Stated another way, the invention tends to reduce the dynamic focusing range somewhat.) Applicant has found that using a window/lens that has a focal length of about one-and-a-half times the distance between itself and the reflector provides suitable reduction of geometrical distortion and enhancement of far field spot size, but without severe degradation of the other performance areas impacted.

I claim:

1. In an apparatus for ultrasonically imaging sections of a body by transmitting ultrasonic energy into the body and determining the characteristics of the ultrasonic energy reflected therefrom, said apparatus including timing means for generating timing signals; energizing/receiving means operative in response to timing signals; and display/record means synchronized with said timing signals for displaying and/or recording image-representative signals from the energizing/receiving means; an improved portable scanning module, comprising:

a fluid-tight enclosure having an ultrasonically-transmissive window which can be placed in contact with the body;

a fluid contained in said enclosure;

transducer means coupled to said energizing/receiving means for converting electrical energy to a beam of ultrasonic energy and for converting reflected ultrasonic energy to electrical signals.

means for focusing the ultrasound beam emanating from said transducer means;

reflective scanning means pivotably mounted in said fluid in the path of said ultrasound beam for effecting scanning of said beam across said body via said window;

said window comprising an acoustic lens for converging the scan of the ultrasound beam incident thereon from within said enclosure, whereby said acoustic lens reduces geometrical distortion of the scan of said ultrasound beam.

2. Apparatus as defined by claim 1 wherein said acoustic lens has a focal length of between one and two times the distance between said reflective scanning means and said acoustic lens.

3. Apparatus as defined by claim 1 wherein said acoustic lens has a focal length of about one-and-a-half times the distance between said reflective scanning means and said acoustic lens.

4. Apparatus as defined by claim 1 wherein said means for focusing the ultrasound beam emanating from said transducer means comprises another acoustic lens, said another acoustic lens contacting said transducer.

5. Apparatus as defined by claim 4 wherein said means for focusing the ultrasound beam emanating from said transducer means comprises aother acoustic lens, said another acoustic lens contacting said transducer.

6. The scanning module as defined by claim 1 wherein said acoustic lens is of a substantially plano-concave shape with the concave surface facing the inside of said enclosure.

7. Apparatus as defined by claim 6 wherein said acoustic lens has a focal length of between one and two times the distance between said reflective scanning means and said acoustic lens.

8. Apparatus as defined by claim 6 wherein said acoustic lens has a focal length of about one-and-a-half times the distance between said reflective scanning means and said acoustic lens.

9. The scanning module as defined by claim 6 wherein said acoustic lens is formed of a rigid plastic material.

10. Apparatus as defined by claim 9 wherein said acoustic lens has a focal length of between one and two times the distance between said reflective scanning means and said acoustic lens.

11. Apparatus as defined by claim 10 wherein said means for focusing the ultrasound beam emanating from said transducer means comprises another acoustic lens, said another acoustic lens contacting said transducer.

12. Apparatus as defined by claim 9 wherein said means for focusing the ultrasound beam emanating from said transducer means comprises another acoustic lens, said another acoustic lens contacting said transducer.

13. Apparatus as defined by claim 9 wherein said acoustic lens has a focal length of about one-and-a-half times the distance between said reflective scanning means and said acoustic lens.

* * * * *